United States Patent [19]
DeToro

[11] Patent Number: 5,545,127
[45] Date of Patent: * Aug. 13, 1996

[54] LATERALLY ADJUSTABLE ANKLE AND FOOT ORTHOSIS

[76] Inventor: William DeToro, 930 Trailwood Dr., Boardman, Ohio 44512

[*] Notice: The term of this patent shall not extend beyond the expiration date of Pat. No. 5,088,479.

[21] Appl. No.: 427,557

[22] Filed: Apr. 24, 1995

[51] Int. Cl.⁶ ..................................................... A61F 5/00
[52] U.S. Cl. .................................................. 602/27
[58] Field of Search .............................. 602/23, 27, 62, 602/65; 128/869, 882

[56] References Cited

U.S. PATENT DOCUMENTS

| | | |
|---|---|---|
| 246,984 | 9/1881 | Stillman ........................... 602/27 |
| 3,171,407 | 3/1965 | Rogers . |
| 3,528,412 | 9/1970 | McDavid . |
| 3,779,654 | 12/1973 | Horne . |
| 3,902,482 | 9/1975 | Taylor . |
| 3,976,059 | 8/1976 | Lonardo . |
| 4,337,764 | 7/1982 | Lerman . |
| 4,771,768 | 9/1988 | Crispin . |
| 4,934,355 | 6/1990 | Porcelli . |
| 4,962,760 | 10/1990 | Jones . |
| 5,088,479 | 2/1992 | DeToro . |
| 5,154,695 | 10/1992 | Farris et al. ......................... 602/27 |
| 5,183,036 | 2/1993 | Spademan ......................... 602/27 X |
| 5,269,748 | 12/1993 | Lonardo . |

Primary Examiner—Richard J. Apley
Assistant Examiner—Kim M. Lee
Attorney, Agent, or Firm—Robert J. Herberger, Esquire

[57] ABSTRACT

An ankle and foot orthosis device for support and selective immobilization of a patient's ankle and foot comprised of a multiple part L-shaped construction with a contoured leg support portion, a foot portion and a heel portion. The heel portion has a resilient two-part construction interconnecting the leg support portion and the foot portion. The two-part interconnecting heel portion includes upper and lower portions with a pivotal connection therebetween to provide incremental angular rotational displacement between the leg support portion and the foot portion.

6 Claims, 2 Drawing Sheets

LATERALLY ADJUSTABLE ANKLE AND FOOT ORTHOSIS

TECHNICAL FIELD

The present invention relates to a therapeutic leg and foot brace used to support the leg and foot of a patient for partial immobilization and, more particularly, to a brace having a two-part interconnecting heel portion to provide selective incremental lateral alignment deviation therebetween.

BACKGROUND OF THE INVENTION

In recent times, thereaputic leg and foot braces of this type typically have an L-shaped construction with a contoured leg support portion, a foot portion and an interconnected heel portion therebetween. Currently the interconnecting heel portion is a one-piece resilient metal alloy member adjustably secured between the leg and foot portion as taught by DeToro, U.S. Pat. No. 5,088,479. The interconnecting heel portion has also been molded to the leg portion and foot portion in a one-piece construction as taught by Lonardo in U.S. Pat. Nos. 5,269,748 and 3,976,054.

Other foot and leg brace configurations are directed to pivoting joints between the leg support and foot portions that allow for horizonal and vertical flexible movement while holding the patient's foot and leg laterally fixed, see for example U.S. Pat. Nos. 4,934,355, 4,962,760 and 4,771,768. Artificial joints for simulating motion of a slide-in-hinge joint of the body in a forward and backward motion while remaining laterally fixed are shown in knee and ankle joint U.S. Pat. Nos. 3,779,654, 3,902,482, 4,337,764 and 3,528,412. An orthotic foot brace having lateral displacement of a foot portion to a leg portion is illustrated in U.S. Pat. No. 3,171,407.

Consequently, a need exists for an improved means for incremental adjustment of the lateral angle between the foot and leg portion in an orthotic brace having a resilient interconnected heel enclosed portion.

OBJECTS AND ADVANTAGES

Accordingly, it is an object of the present invention to provide a lateral adjustment between the upper leg portion and the foot portion of an orthotic brace by utilizing an adjustable two-part resilient interconnecting element. A second object of the present invention is to provide an absolute limit of right and left lateral adjustment, as well as predetermined incremental positions in relation to the otherwise fixed vertical axis of the device.

Other objects and features of the present invention will be obvious to those of skill in the art. It should be noted, however, that the drawings are designed for the purpose of illustration only and not as a definition of the limits of the instant invention, for which reference should be made to the claims appended hereto.

SUMMARY OF THE INVENTION

The invention is described as an orthotic foot brace generally comprised of a leg portion, a foot portion and an interconnecting heel portion. In this invention, the foot portion may have a walking pad and a toe extension portion. Further, the interconnecting heel portion has overlapping pivotal end portions connected by a pivot and slide arrangement. The overlapping pivotal end portions have a central pivot point. Opposing C-shaped or arcuate slide openings in one of the overlapping end portions communicate with a pair of limit stop fasteners connected to the other overlapping end portion, thereby limiting lateral angular inclination between the foot portion and the leg portion.

DESCRIPTION OF THE PREFERRED EMBODIMENT

Figure 1:
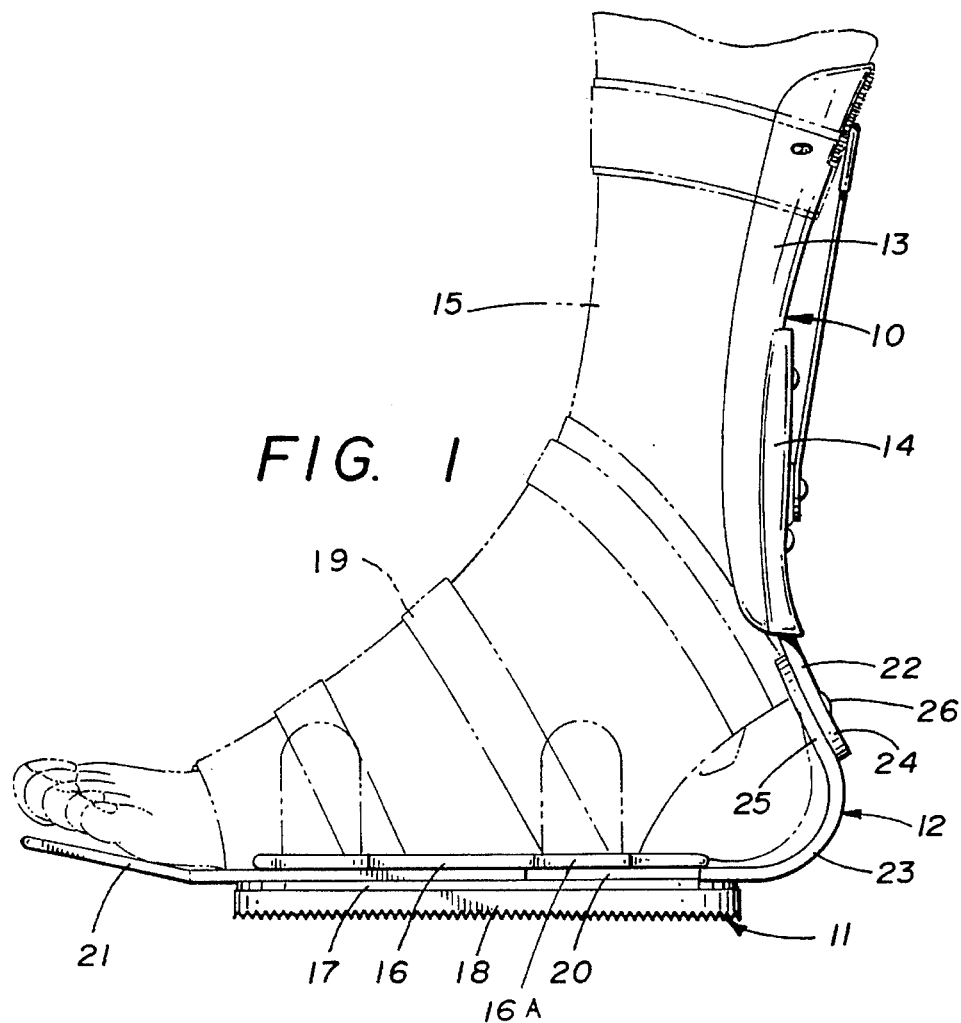
FIG. 1 is a side elevational view of the present invention with a patients foot secured therein.
Figure 3:
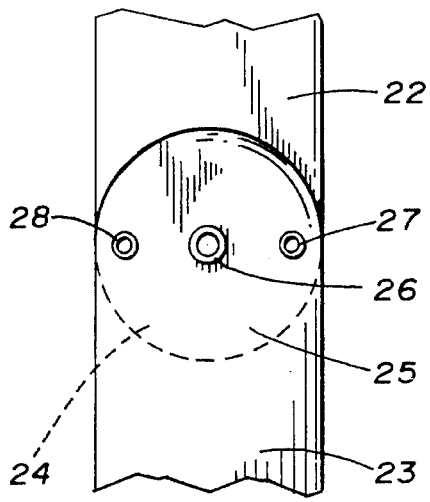
FIG. 3 is an enlarged partial front elevational view of the pivot joint of the invention.
Figure 2:
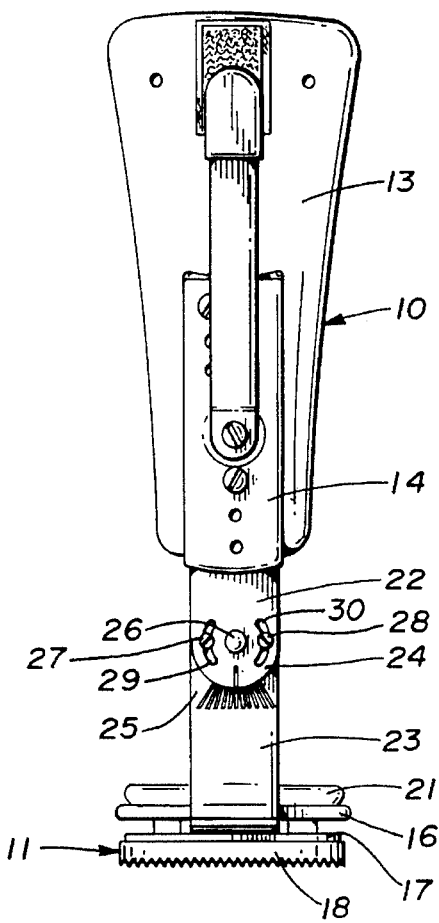
FIG. 2 is a rear elevational view of the invention.

Referring to FIGS. 1 and 2 of the drawings, the orthotic brace of the invention, comprising a leg portion 10, a foot portion 11 and an interconnecting heel portion 12 extending therebetween can be seen. The leg portion has an enlarged transversely contoured leg support 13 with a recessed elongated channel 14 formed inwardly on one end thereof.

In practice, the leg and foot portions 10 and 11 are made of synthetic plastic resin material so that they may be molded or formed into desirable contours required for engagement with a patient's leg 15 shown in broken lines in FIG. 1 of the drawings. The foot portion 10 has a foot pad 16 secured to an attachment base 17 having a resilient walking pad 18 secured thereto. The foot pad 16 has apertured tabs 16A therein to which is secured a fabric foot engagement enclosure 19 shown in broken lines in FIG. 1 of the drawings. A mounting pocket 20 extends inward from the bottom of the foot pad 16 for engagement of the interconnected heel portion 12 between the foot pad 16 and attachment base 17. A toe extension member 21 is adjustably secured to the foot pad 16 opposite the mounting pocket 20 between the foot pad 16 and attached base 17.

Figure 4:
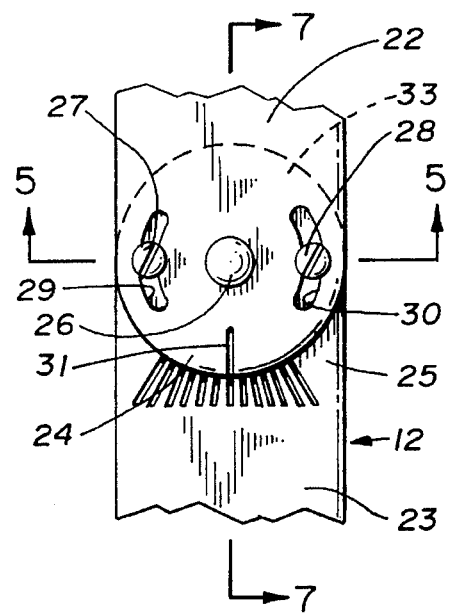
FIG. 4 is an enlarged partial rear elevational view of the pivot joint shown in FIG. 3.

The interconnecting heel portion 12 is comprised of a first and second pivot bearing elements 22 and 23 of a resilient metal alloy or suitable composite material. Referring to FIG. 4 of the drawings, the overlapping portions of the respective first and second pivot bearing elements 22 and 23 define a generally circular configuration at 33. The first pivoted bearing element 22 has a slight longitudinally curved configuration extending from and secured by fasteners within the elongated channel 14 of the leg portion 10. The first pivot bearing element 22 has a first pivot engagement free end 24 at the end opposite the portion secured to the leg portion as best seen in FIGS. 2, 4 and 6.

Figure 5:
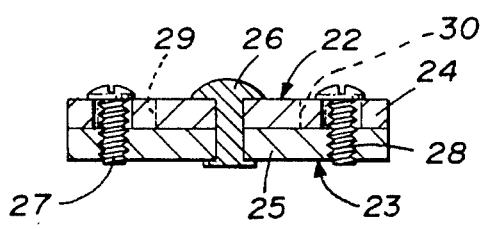
FIG. 5 is an enlarged pivotal cross-sectional view on lines 5—5 of FIG. 4.
Figure 7:
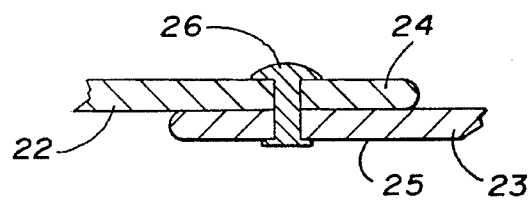
FIG. 7 is an enlarged partial cross-sectional view on lines 7—7 of FIG. 4.

The second pivot bearing element 23 extends from and is secured by fasteners within the mounting pocket 20 hereinbefore described. The second pivot bearing element 23 has a curved generally L-shaped configuration with an apertured pivot engagement free end 25 in an overlapping aligned relationship with the respective first pivot engagement free end 24. A pivot pin 26 interconnects the overlapping pivot free ends 24 and 25 by extending through centrally positioned and aligned apertures therein, as best seen in FIGS. 4, 5, and 7.

A pair of oppositely disposed stop fasteners 27 and 28 are threadably secured into the apertures in the free end 25 of the second pivot bearing element 23. The stop fasteners 27 and 28 are aligned through the respective arcuate slots 29 and 30 in the first overlapping free end portion 24 of the first pivot bearing element 22, as best shown in FIGS. 4 and 5.

Figure 6:
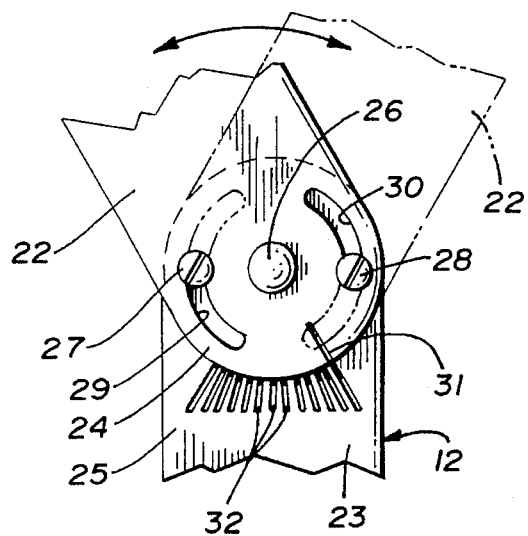
FIG. 6 is an enlarged partial rear elevational view of the pivoting joint of the invention in full lateral disposed alignment.

In use, the first pivot bearing element 22 can be disposed laterally in relation to the second pivot bearing element 23 and its interconnected foot portion 11 as illustrated in FIG. 6 of the drawings in solid and broken lines. The degree of lateral movement therebetween can be incrementally adjusted and measured by aligning an indicator groove 31 on the free end 24 of the first pivot bearing element 22 with the multiple incrementally spaced indicator grooves 32 formed on the free end 25 of the second bearing element 23. Once the desired degree of lateral alignment is achieved, the limit stop fasteners 27 and 28 are tightened thereby locking the first and second pivot bearing elements 22 and 23 together.

It will be evident to those skilled in the art that various changes and modifications may be made therein without departing from the spirit of the invention. Accordingly, the scope of the instant invention should not be defined by the embodiment shown above, but rather by the claims appended hereto and their equivalence.

Therefore, what is claimed is:

1. A laterally adjustable leg and foot brace for use on a patient, said brace comprised of:
    a. a foot portion connected to a substantially rigid leg portion by a resilient interconnecting heel portion, the interconnecting heel portion positioned behind the patient's heel, said interconnecting heel portion being curved to provide a gap between the patient's heel and the interconnecting heel portion to permit lateral visibility of the gap and the patient's heel;
    b. said interconnecting heel portion having a first element and a second element, each element having a pivotal end, the pivotal end portions overlapping and being adjustably secured to each other, the pivotal end portion of the first element is secured to the pivotal end of the second element by a pivot pin, the overlapping of the pivotal end portions being aligned substantially lateral to the patient's ankle when the posterior region of the lower leg and the sole of the patient's foot are in supporting contact with said leg portion and said foot portion, respectively;
    c. the pivotal end of the first element having an arcuate slot therethrough;
    d. the pivotal end of the second element having a stop fastener secured thereto, the stop fastener being aligned with the arcuate slot through the pivotal end of the first element, so that when the stop fastener is tightened through the arcuate slot against the first element to the second element, the interconnecting heel portion is prevented from laterally rotating; and
    e. the pivotal end of the first element having an indicator groove and the pivotal end of the second element having a plurality of incrementally spaced indicator grooves for measuring the degree of pivotal rotation between the first element and the second element.

2. The brace set forth in claim 1, wherein the stop fastener is a screw which is secured to a threaded hole through the second element.

3. The brace set forth in claim 1, wherein the pivotal end of the first element has at least two arcuate slots therethrough and the pivotal end of the second element having an equal number of stop fasteners secured thereto, each stop fastener being aligned with one of the arcuate slots.

4. The brace set forth in claim 1, further comprised of an attachment base, a resilient walking pad secured to said attachment base, an adjustable toe extension member, and a foot engagement enclosure for securing the patient's foot to the foot portion and leg portion.

5. The brace set forth in claim 1, wherein the first element is secured to the leg portion and the second element is secured to the foot portion.

6. The brace set forth in claim 1 or 3, wherein the pivot pin is connected to the second element and the pivot pin extends through an aperture in the first element.

* * * * *